(12) United States Patent
Timmermann et al.

(10) Patent No.: US 6,177,580 B1
(45) Date of Patent: Jan. 23, 2001

(54) CONJUGATED LINOLENIC ACID-BASED SYNTHETIC TRIGLYCERIDES

(75) Inventors: Franz Timmermann, Illertissen; Rolf Gaupp, Dietenheim; Juergen Gierke; Rainer Von Kries, both of Illertissen; Wolfgang Adams, Meckenbeuren; Andreas Sander, Illertissen, all of (DE)

(73) Assignee: Henkel Kommanditgesellschaft auf Aktien, Duesseldorf (DE)

( * ) Notice: Under 35 U.S.C. 154(b), the term of this patent shall be extended for 0 days.

(21) Appl. No.: 09/423,054

(22) PCT Filed: Apr. 21, 1998

(86) PCT No.: PCT/EP98/02332

§ 371 Date: Oct. 29, 1999

§ 102(e) Date: Oct. 29, 1999

(87) PCT Pub. No.: WO98/49129

PCT Pub. Date: Nov. 5, 1998

(51) Int. Cl.[7] ............... C07C 51/00; C07C 3/00; C11C 1/00; C11C 3/00; C07B 35/08
(52) U.S. Cl. ............ 554/169; 554/173; 554/126
(58) Field of Search .................. 554/169, 173, 554/126

(56) References Cited

U.S. PATENT DOCUMENTS

| 3,984,444 | 10/1976 | Ritz et al. | 260/405.6 |
|---|---|---|---|
| 5,466,843 | * 11/1995 | Cooper et al. | 554/149 |
| 5,585,399 | 12/1996 | Hong et al. | 514/546 |

FOREIGN PATENT DOCUMENTS

| 21 55 727 | 5/1973 | (DE) . |
|---|---|---|
| 0 579 901 | 1/1994 | (EP) . |
| 6-276939 | 10/1994 | (JP) . |
| WO94/16690 | 8/1994 | (WO) . |
| WO96/06605 | 3/1996 | (WO) . |
| WO96/34846 | 11/1996 | (WO) . |
| WO97/18320 | 5/1997 | (WO) . |

OTHER PUBLICATIONS

Chin et al, Dietary Sources of Conjugated Dienoic Isomers of Linoleic Acid, a Newly Recognized Class of Anticarcinogens, Journal of Food Composiiton and Analysis, Sep. 1992.*
Nutrition, vol. 19/ NR.6 (1995).
J. Food Compos. Anal.5, 185–197.
Carcinogenesis 8, 1881–1887 (1987).
Cancer Lett. 63, 125–133 (1992).
Antherosclerosis 108, 19–25 (1994).
Agric. Biol. Chem., 47 (10), 2243–2249 1983.
JAOCS, vol. 50 pp. 459–461.
JOACS, vol. 73, No. 11 (1996) pp. 1415–1420.
JAOCS, vol. 59, No. 3 (1982) pp. 124–129.

* cited by examiner

Primary Examiner—Deborah D. Carr
Assistant Examiner—Diedra Faulkner
(74) Attorney, Agent, or Firm—John E. Drach; Steven J. Trzaska

(57) ABSTRACT

A process for making synthetic triglycerides involving: (a) providing a reaction component selected from the group consisting of glycerol, a triglyceride, and mixtures thereof; (b) providing a fatty acid mixture containing at least 50% by weight, based on the weight of the fatty acid mixture, of conjugated linoleic acid; (c) providing an inert gas atmosphere; (d) combining the reaction component with the fatty acid mixture, in the inert atmosphere, to form a reaction mixture; and (e) heating the reaction mixture to a temperature of from 180 to 240° C., at a heating rate of from 0.5 to 3 K per minute, thus forming the synthetic triglyceride.

16 Claims, No Drawings

CONJUGATED LINOLENIC ACID-BASED SYNTHETIC TRIGLYCERIDES

BACKGROUND OF THE INVENTION

This invention relates to synthetic triglycerides containing $C_{6-24}$ fatty acid residues, with the proviso that at least one residue is a conjugated linoleic acid residue, and to a process for the production of the triglycerides. The invention also relates to the use of the triglycerides in foods and pharmaceutical products.

Polyunsaturated ω-3 and ω-6 fatty acids, such as α-linolenic acid and linoleic acid, are among the fatty acids essential to mammals and human beings. Besides linoleic acid, other isomeric octadecadienoic acids occur in nature. They are distinguished by conjugated double bonds at carbon atoms 9 and 11, 10 and 12 and 11 and 13. These isomeric octadecadienoic acids are collectively referred to in the scientific literature as conjugated linoleic acids (abbreviation: CLAs) and have recently attracted increasing attention (NUTRITION, Vol. 19, No. 6, 1995).

Conjugated linoleic acids are present as constituents in various foods. Their main source are animal foods although significant quantities of CLA are also present in milk and milk products. In addition, CLAs have been found in various oils and fats, the concentration in vegetable oils being significantly lower than the concentration in animal fats (J. Food Compos. Anal. 5, 185–197 (1992)).

Various working groups have reported on the significance of CLAs to the organism. Recently, Shultz et al. reported on the inhibiting effect on the in-vitro growth of human cancer cells (Carcinogenesis 8, 1881–1887 (1987) and Cancer Lett. 63, 125–133 (1992)).

In in vitro tests, CLAs were tested for their effectiveness against the growth of malignant human melanomas, colon and breast cancer cells. In the culture media, there was a significant reduction in the growth of the cancer cells treated with CLAs by comparison with control cultures. The mechanism by which CLAs exert anticarcinogenic activity is unknown. In addition, CLAs have a strong antioxidative effect so that, for example, the peroxidation of lipids can be inhibited (Atherosclerosis 108, 19–25 (1994)).

Investigations have also been conducted, for example, into the addition of conjugated linoleic acid to foods for the purpose of color stabilization (JP 06/276939 A2).

The use of conjugated linoleic acid in animal feeds and, in this connection, also in human nutrition is known, for example, from WO 96/06605. This application is concerned with reducing body fat content in animal nutrition. In the statement of problem, the specification also mentions the possibility of application to human beings. In particular, it mentions the use of a fatty emulsion containing 0.5 to 2% by weight of conjugated linoleic acid for oral or intravenous administration to human beings.

EP 0 579 901 B relates to the use of conjugated linoleic acid for avoiding loss of weight or for reducing increases in weight or anorexia caused by immunostimulation in human beings or animals.

WO 94/16690 is concerned with improving the efficiency of food utilization in animals by administering an effective quantity of conjugated linoleic acid.

In connection with the many positive effects of conjugated linoleic acid, as demonstrated in intensive studies, particularly on animals and tissue cultures, the use of conjugated linoleic acid in foods for human consumption has also been discussed. However, the use of free conjugated linoleic acid in foods and pharmaceutical products is limited by the fact that, on the one hand, unwanted reactions with other food constituents can occur where free conjugated linoleic acid is incorporated in complex foods and, on the other hand, by the unpleasant taste and odor of conjugated linoleic acid which can lead to non-acceptance by the consumer. Another disadvantage is that free fatty acids are covered by food additive legislation so that their use in foods is restricted.

Accordingly, the complex problem addressed by the present invention was to find a substitute for conjugated linoleic acid, above all in human nutrition and also for pharmacological use. On the one hand, this substitute would have better organoleptic properties than conjugated linoleic acid and, on the other hand, would lend itself to incorporation in foods without initiating secondary reactions.

DESCRIPTION OF THE INVENTION

Accordingly, the present invention relates to synthetic triglycerides corresponding to formula (I):

in which $R^1$, $R^2$ and $R^3$ independently of one another represent $C_{6-24}$ fatty acid residues, with the proviso that at least one substituent $R^1$, $R^2$ or $R^3$ is a conjugated linoleic acid residue.

The present invention also relates to a process for the production of synthetic triglycerides by esterification of glycerol or transesterification of triglycerides with fatty acid mixtures by methods known from the prior art, with the proviso that at least 50% by weight of conjugated linoleic acid is used in the fatty acid mixture, the reaction is carried out in an inert gas atmosphere and heating to the reaction temperature is preferably carried out at a heating rate of 0.2 to 10 K per minute.

The present invention also relates to the use of the triglycerides according to the invention in foods and/or as active substances for the production of pharmaceutical products.

It has surprisingly been found that the triglycerides according to the invention are comparable with pure conjugated linoleic acid in their antioxidative and color-stabilizing effect in foods. In addition, they may readily be incorporated in foods and pharmaceutical products without initiating any secondary reactions. In particular, their lipophilic character enables then to be readily incorporated in fat-containing products. The triglycerides according to the invention are also readily absorbed by the animal or human organism. At the same time, they have an almost neutral taste and odor They are therefore far superior in their organoleptic properties to free conjugated linoleic acid. This means, for example, that the triglycerides can be used in larger quantities in foods. Even food supplements consisting of pure triglyceride of conjugated linoleic acid can be taken by mouth by virtue of their outstanding organoleptic properties. Another advantage is that they do not come under food additive legislation, in other words there are no restrictions on their incorporation in foods.

It has also been found that, surprisingly, the triglycerides according to the invention can also readily be obtained in high yields, more particularly by the direction esterification of glycerol with conjugated linoleic acid, providing the reaction is carried out in an inert gas and providing a low heating rate is maintained.

Triglycerides

In the triglycerides of formula (I) according to the invention, at least one of the substituents $R^1$, $R^2$ or $R^3$ is a conjugated linoleic acid residue while the other constituents represent $C_{6-24}$ fatty acid residues. However, triglycerides which, on a statistical average, contain more than 2 conjugated linoleic acid residues per triglyceride are particularly preferred, triglycerides in which the substituents $R^1$, $R^2$ and $R^3$ represent a conjugated linoleic acid residue being most particularly preferred. In the context of the present invention, triglycerides are also understood to be the technical mixtures of mono-, di- and triglycerides which are obtained in particular in the direct esterification of glycerol with conjugated linoleic acid. A typical composition which is particularly preferred and which is obtained in the process according to the invention, more particularly in the esterification of glycerol with conjugated linoleic acid, contains 60 to 98% by weight and preferably 80 to 98% by weight of a triglyceride of conjugated linoleic acid, 1 to 40 and preferably 1 to 20% by weight of a diglyceride of conjugated linoleic acid and at most 2% by weight and preferably at most 1% by weight of a monoglyceride of conjugated linoleic acid. At the same time, the glyceride to be used in accordance with the invention has an acid value of at most 5 and preferably of at most 3, a hydroxyl value below 40 and preferably below 30 and a peroxide number below 4 and preferably below 2.

Fatty Acids

Fatty acids in the context of the present invention are aliphatic carboxylic acids corresponding to formula (II):

$$R^4CO\text{—}OH \qquad (II)$$

in which $R^4CO$ is an aliphatic, linear or branched acyl group containing 6 to 24 carbon atoms and 0 and/or 1, 2 or 3 double bonds.

Typical examples are caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and the technical mixtures thereof obtained, for example, in the pressure hydrolysis of natural fats and oils, in the reduction of aldehydes from Roelen's oxosynthesis or in the dimerization of unsaturated fatty acids.

Technical $C_{12-18}$ fatty acids such as, for example, coco-fatty acid, palm oil fatty acid, palm kernel oil fatty acid or tallow fatty acid, are preferred.

According to the invention, conjugated linoleic acid is preferably understood to be the main isomers 9,11-octadecadienoic acid and 10,12-octadecadienoic acid, but also includes the isomer mixtures normally obtained in the production of conjugated linoleic acid.

Transesterification

The fatty acid glycerides to be used as starting materials in accordance with the invention may be the usual natural vegetable or animal fats and oils. These include, for example, palm oil, palm kernel oil, cottonseed oil, rapeseed oil, coconut oil, peanut oil, olive oil, linseed oil, babassu oil, tea oil, olive kernel oil, meadow foam oil, chaulmoogra oil, coriander oil, soybean oil, castor oil, lard oil, beef tallow, lard, fish oil and also sunflower oil and rapeseed oil from old and new plants. The main constituents of these fats and oils are glycerides of various types of fatty acids which contain considerable quantities of impurities such as, for example, aldehyde compounds, phospholipid compounds and free fatty acids. These materials may be used either directly or after purification. In some cases, it is particularly advisable to esterify the free fatty acids with lower alcohols in a preliminary reaction. These triglycerides are transesterified with fatty acid mixtures containing at least 50, more especially 70 to 100% by weight of conjugated linoleic acid in an inert gas atmosphere by methods known from the prior art, i.e. by acidic and/or basic transesterification. Nitrogen is preferably used as the inert gas. The reaction is preferably carried out at a temperature of 180 to 240° C. In one particularly preferred embodiment, heating to that temperature is carried out at a low rate of 0.2 to 10 and preferably 0.5 to 3 K per minute. Suitable catalysts are any of the usual catalysts known from the prior art for esterification or transesterification reactions. Such catalysts are, for example, alkali metal and/or alkaline earth metal alcoholates or hydroxides, more especially sodium methanolate and sodium glycerate. It is also preferred to use acetates, such as zinc and/or magnesium acetate, or even titanates and, in particular, tin compounds, organotin compounds, such as dibutyl tin diacetate for example, or tin salts.

Esterification

In one particularly preferred embodiment, the triglycerides according to the invention are not produced by transesterification, but rather by the direct esterification of glycerol with a fatty acid mixture containing at least 50 and preferably 70 to 100% by weight of conjugated linoleic acid in an inert gas atmosphere, again preferably nitrogen, by methods known from the prior art. The esterification of glycerol with 100% by weight of conjugated linoleic acid is particularly preferred. Technical mixtures of mono-, di- and triglycerides of conjugated linoleic acid are normally obtained. According to the invention, these mixtures may be used both directly and after further purification. The foregoing observations on the temperature, heating rate and catalyst used for the transesterification apply similarly to esterification.

After esterification or transesterification, 0.01 to 1% by weight of an antioxidant is preferably added. In another preferred embodiment, the triglyceride obtained is purified using a thin-layer evaporator, after which another 0.01 to 1% by weight of an antioxidant is added.

Antioxidants

Antioxidants in the context of the present invention are any of the usual natural antioxidants which are used in particular in pharmaceutical products and in foods, including vitamin C and vitamin C derivatives such as, for example, ascorbyl palmitate, carotinoids, rosemary extracts and/or synthetic antioxidants such as, for example, BHA, BHT, TBHQ or gallates and, in particular, various vitamin E derivatives, such as Coviox® T 70 for example.

Uses

The triglycerides according to the invention are particularly suitable for use in foods, preferably so-called functional foods, and in pharmaceutical products, more especially as a supporting agent in the treatment of tumors or even in the treatment of patients suffering from catabolic conditions. Since the physiological properties of the triglycerides according to the invention are comparable with those of free conjugated linoleic acid both in human beings and in animals, the triglycerides are suitable for use in all those areas which are already known from the literature for conjugated linoleic acid.

EXAMPLES

Production of a Conjugated Linoleic Acid Triglyceride

Example 1

92.1 kg of glycerol and 841.5 kg of conjugated linoleic acid were preheated under nitrogen to around 80° C. and introduced into a reactor, after which 0.62 kg of tin grindings were added with stirring. The reactor was then evacuated to 30 mbar, stirred for 10 minutes and blanketed with nitrogen. Heating was carried out under nitrogen at a rate of 1 K per minute, the temperature reaching 150° C. after 1 hour. At the same time, the pressure was reduced to 800 mmbar. The temperature was then increased to 210° C. over a period of another hour and the reaction mixture was stirred at that temperature for 2 hours. The reaction mixture was then re-evacuated to 30 mmbar over a period of 30 minutes and stirred until an acid value of 15 had been reached. The reaction mixture was then cooled in vacuo to 90° C. and purged with nitrogen, after which phosphoric acid was added to precipitate the catalyst. After stirring for 15 minutes and after the addition of Perlite, the reaction mixture was filtered through a filter press into a nitrogen-purged receiver to which 0.1% by weight of Coviox T-70 was added as stabilizer.

Example 2

The procedure was as in Example 1, except that the crude product was deodorized in a thin-evaporator at 230° C. in the presence of stripping steam. Another 0.2% by weight of Coviox T-70 was added to the end product for stabilization.

Glyceride Composition

Example 3

A glyceride prepared as described in Example 1 has the following composition:

| | |
|---|---|
| triglyceride of conjugated linoleic acid: | 95% by weight |
| diglyceride of conjugated linoleic acid | 3% by weight |
| monoglyceride of conjugated linoleic acid: | 2% by weight |

The acid value was 2, the hydroxyl value 25 and the peroxide number 2.

What is claimed is:

1. A process for making synthetic triglycerides comprising:
    (a) providing a reaction component selected from the group consisting of glycerol, a triglyceride, and mixtures thereof;
    (b) providing a fatty acid mixture containing at least 50% by weight, based on the weight of the fatty acid mixture, of conjugated linoleic acid;
    (c) providing an inert gas atmosphere;
    (d) combining the reaction component with the fatty acid mixture, in the inert atmosphere, to form a reaction mixture; and
    (e) heating the reaction mixture to a temperature of from 180 to 240° C., at a heating rate of from 0.5 to 3 K per minute, thus forming the synthetic triglyceride.

2. The process of claim 1 wherein the reaction component is glycerol.

3. The process of claim 1 wherein the reaction component is a triglyceride.

4. The process of claim 1 wherein the fatty acid mixture contains from 70 to 100% by weight, based on the weight of the fatty acid mixture, of conjugated linoleic acid.

5. The process of claim 1 further comprising adding a catalyst to the reaction mixture.

6. The process of claim 1 further comprising adding from 0.01 to 1% by weight, based on the weight of the synthetic triglyceride, of an antioxidant to the synthetic triglyceride.

7. The process of claim 1 further comprising purifying the synthetic triglyceride using a thin-layer evaporator in order to form a purified synthetic triglyceride.

8. The product of the process of claim 1.

9. The product of the process of claim 2.

10. The product of the process of claim 3.

11. The product of the process of claim 4.

12. The product of the process of claim 5.

13. The product of the process of claim 6.

14. The product of the process of claim 7.

15. A food product containing the synthetic glyceride of claim 1.

16. A pharmaceutical product containing the synthetic glyceride of claim 4.

* * * * *